(12) United States Patent
Viergutz et al.

(10) Patent No.: US 6,177,570 B1
(45) Date of Patent: Jan. 23, 2001

(54) METHOD FOR PRODUCING AROMATIC BISIMIDES

(75) Inventors: Wolfgang Viergutz; Stefan Koser, both of Ludwigshafen (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/381,051

(22) PCT Filed: May 4, 1998

(86) PCT No.: PCT/EP98/02621

§ 371 Date: Sep. 14, 1999

§ 102(e) Date: Sep. 14, 1999

(87) PCT Pub. No.: WO98/52924

PCT Pub. Date: Nov. 26, 1998

(30) Foreign Application Priority Data

May 16, 1997 (DE) ................................. 197 20 803

(51) Int. Cl.[7] ...................... C07D 221/14; C07D 209/48
(52) U.S. Cl. ......................... 546/99; 546/100; 548/461; 548/462
(58) Field of Search .............. 546/99; 548/461, 548/462

(56) References Cited

U.S. PATENT DOCUMENTS 5,488,110  1/1996  Sun ...................................... 546/100

FOREIGN PATENT DOCUMENTS

| 2082023 | 5/1993 | (CA) . |
| 540 975 | 5/1993 | (EP) . |
| 93/12092 | 6/1993 | (WO) . |
| 94/02466 | 2/1994 | (WO) . |
| 96/25400 | 8/1996 | (WO) . |

OTHER PUBLICATIONS

Chem. Rev. vol. 70, No. 4, Hargreaves et al., 439–469 (1970).
JP Abstract 5 8096–066 (1983).

*Primary Examiner*—Evelyn Mei Huang
(74) *Attorney, Agent, or Firm*—Keil & Weinkauf

(57) ABSTRACT

Bisimides of the formula I

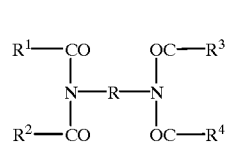

where $R^1$, $R^2$, $R^3$ and $R^4$ have the meanings stated in the description, are prepared in a process in which the corresponding dicarboxylic anhydrides of the formulae II and III

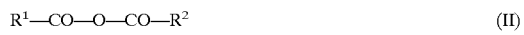

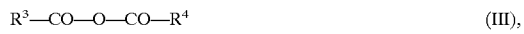

are reacted with an amine of the formula $H_2N$—R—$NH_2$ in the presence of a tertiary amine.

3 Claims, No Drawings

METHOD FOR PRODUCING AROMATIC BISIMIDES

This application is the national phase of PCT/EP98/02621, filed May 4, 1998.

The present invention relates to a novel process for preparing aromatic bisimides.

Cyclic imides are normally prepared from cyclic carboxylic anhydrides and ammonia or a primary amine, (Chem.Rev. 70 (1970) 439–469). Other methods are reaction of dicarboxylic acids and ammonia or primary amines at elevated temperature (200° C.) or reaction of diesters with ammonia or primary amines in the presence of sodium ethanolate. Furthermore, for example, maleimides are synthesized in various solvents such as DMF, dioxane or dimethylacetamide with the addition of catalytic amounts N-methylmorpholine (JP 5 8096-066-A).

To prepare aromatic bisimides such as bisnaphthalimides, naphthalic anhydrides are heated with polyamines in solvents such as DMSO, DMF, THF or ethanol (WO 94/02466). The synthesized bisnaphthalimides were purified by chromatography. J. H. Sun likewise used ethanol as solvent to prepare bisnaphthalimides (U.S. Pat. No. 5,488,110). However, this synthetic method cannot be carried out on a larger scale because the purification of the product by column chromatography is too elaborate.

A process with which naphthalic and phthalic anhydrides can be converted in a simple manner into their bisimides has now been found.

The invention relates to a process for preparing bisimides of the formula I

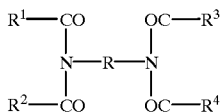

(I)

where

R is —$Alk^1$—NH—$Alk^2$—(NH—$Alk^3$)$_a$—, where $Alk^1$, $Alk^2$ and $Alk^3$ are $C_{2-6}$-alkylene radicals, and a is 0 or 1, $R^1$+$R^2$ together are

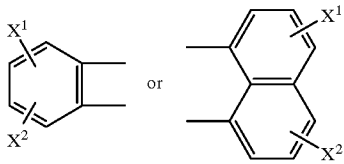

and $R^3$+$R^4$ together are

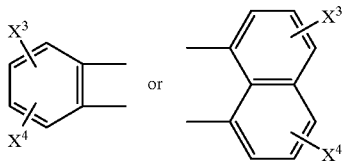

where $X^1$ and $X^2$, which may be identical or different, are hydrogen or halogen atoms, nitro groups, amino groups which are unsubstituted or substituted by 1 or 2 $C_{1-4}$-alkyl radicals, or hydroxyl groups, mercapto groups or $C_{1-4}$-alkyl groups, and $X^3$ and $X^4$, which may be identical or different, are hydrogen or halogen atoms, amino groups which are unsubstituted or substituted by 1 or 2 $C_{1-4}$-alkyl radicals, or hydroxyl groups, mercapto groups or $C_{1-4}$-alkyl groups, by reacting the corresponding dicarboxylic anhydrides of the formulae II and III $R^1$—CO—O—CO—$R^2$ (II)
$R^3$—CO—O—CO—$R^4$ (III)

where $R^1$, $R^2$, $R^3$ and $R^4$ have the abovementioned meanings, with an amine of the formula $H_2N$—R—$NH_2$, where R has the same meaning as above, wherein the reaction is carried out in the presence of a tertiary amine.

Suitable starting compounds of the formulae II and III are, in particular, unsubstituted or substituted naphthalic anhydrides.

$X^1$ and $X^2$, which may be identical or different, are preferably hydrogen, fluorine, chlorine or bromine atoms, amino groups which are unsubstituted or substituted by 1 or 2 methyl radicals, or $C_{1-4}$-alkyl groups. It is particularly preferred for groups $X^1$ to be a hydrogen atom and $X^2$ to be a hydrogen atom or an amino group.

The same applies correspondingly to the radicals $X^3$ and $X^4$.

The radicals $X^1$–$X^4$ are preferably located in the m or p position on the rings. The m position is particularly preferred.

It is preferred for $X^1$ and $X^3$, and $X^2$ and $X^4$, to be identical.

Particularly suitable alkylene groups $Alk^1$, $Alk^2$ and $Alk^3$ are those having 3 or 4 carbon atoms. a is preferably 0.

Suitable tertiary amines for the reaction are: triethylamine, diisopropylethylamine, dimethylcyclohexylamine and N—$C_{1-4}$-alkyl-morpholines. Of these, the N—$C_{1-4}$-alkylmorpholines and specifically N-methylmorpholine, are particularly emphasized.

The tertiary amine usually also serves as solvent for the reaction. However, it is also possible to add other solvents such as secondary and tertiary alcohols having up to 6, preferably up to 4, carbon atoms, dioxane, tetrahydrofuran or toluene. It is preferred not to use an additional solvent.

The anhydrides II and III are reacted with the amines in a molar ratio of about 2:1.

The amount of tertiary amine can be varied within a wide range. As a rule, the amount of tertiary amine is sufficient to dissolve the reactants completely therein. However, small amounts of tertiary amine also suffice.

As a rule, the reaction is started at 15–30° C., and the temperature is increased slowly to the reflux temperature. The reaction is complete after about 2 to 4 hours depending on the rate of increase of the temperature.

The product can be isolated from the reaction mixture in a simple manner by partial concentration of the mixture and subsequent precipitation at from 0 to 5° C. The product obtained in this way already has high purity. The product can, if required, be further purified by recrystallization.

The novel process has the advantage by comparison with known processes that it is very easy to carry out, even on the industrial scale, making the compounds I available very satisfactorily.

The compounds I are suitable, for example, for quenching the fluorescence generated by anionic optical brighteners. The naphthalimides display carcinostatic effects.

EXAMPLE 1

At room temperature, 1.89 kg (11.75 mol) of 1,3-bis(2-aminoethylamino)propane, 4.80 kg (23.5 mol, 97% pure) of naphthalic anhydride and 29 l of N-methylmorpholine were placed in a 50 l reactor. The temperature was then increased to 38° C. over the course of 15 min. The mixture was stirred at this temperature for 2 h and then slowly heated to the reflux temperature and kept at this for 1 h. Then 5.8 l were distilled off. The reaction mixture was filtered at about 90° C. and slowly cooled to 0–5° C. The resulting precipitate was filtered off, washed with ice-cold methanol and dried under reduced pressure. The yield was 6.63 kg of N,N'-bis[2-(1,8-naphthalimido)ethyl]-1,3-diaminopropane, m.p. 160° C.

EXAMPLE 2

Example 1 was repeated, but the reaction took place in a mixture of 29 l of N-methylmorpholine and 5 l of ethanol. The yield was 6.26 kg.

The following compounds can be prepared as in Example 1:

We claim:

1. A process for preparing bisimides of the formula I

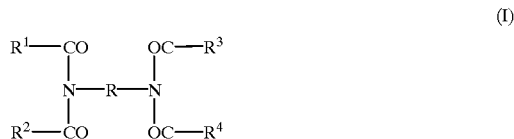

where

R is —$Alk^1$—NH—$Alk^2$—(NH—$Alk^3$)$_a$—, where $Alk^1$, $Alk^2$ and $Alk^3$ are $C_{2-6}$-alkylene radicals, and a is 0 or 1,

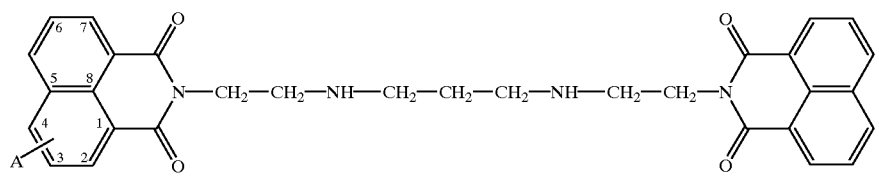

| Example | A |
| --- | --- |
| 3 | 2-OH |
| 4 | 3-OH |
| 5 | 4-OH |
| 6 | 3-$NO_2$ |
| 7 | 4-$NO_2$ |
| 8 | 2-$CH_3$ |
| 9 | 3-Br |

| Example | F | G |
| --- | --- | --- |
| 10 | H | H |
| 11 | H | t-$C_4H_9$ |
| 12 | F | F |

$R^1+R^2$ together are

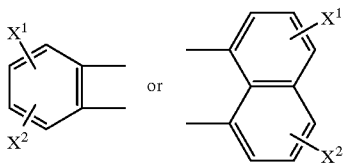

and $R^3+R^4$ together are

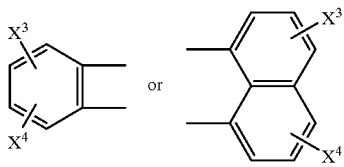

where $X^1$ and $X^2$, which may be identical or different, are hydrogen or halogen atoms, nitro groups, amino groups which are unsubstituted or substituted by 1 or 2 $C_{1-4}$-alkyl radicals, or hydroxyl groups, mercapto groups or $C_{1-4}$-alkyl groups, and $X^3$ and $X^4$, which may be identical or different, are hydrogen or halogen atoms, amino groups which are unsubstituted or substituted by 1 or 2 $C_{1-4}$-alkyl radicals, or hydroxyl groups, mercapto groups or $C_{1-4}$-alkyl groups, by reacting the corresponding dicarboxylic anhydrides of the formulae II and III $$R^1-CO-O-CO-R^2 \qquad (II)$$

$$R^3-CO-O-CO-R^4 \qquad (III),$$

where $R^1$, $R^2$, $R^3$ and $R^4$ have the abovementioned meanings, with an amine of the formula $H_2N-R-NH_2$, where R has the same meaning as above, wherein the reaction is carried out in the presence of a tertiary amine.

2. A process as claimed in claim 1, wherein the reaction is carried out in an $N-C_{1-4}$-alkylmorpholine.

3. A process as claimed in claim 1, wherein the reaction is carried out in N-methylmorpholine.

* * * * *